United States Patent
Konry et al.

(10) Patent No.: US 11,131,673 B2
(45) Date of Patent: Sep. 28, 2021

(54) LIVE SINGLE-CELL BIOASSAY IN MICRODROPLETS

(71) Applicant: Northeastern University, Boston, MA (US)

(72) Inventors: Tania Konry, Boston, MA (US); Saheli Sarkar, Boston, MA (US); Pooja Sabhachandani, Boston, MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 15/965,841

(22) Filed: Apr. 27, 2018

(65) Prior Publication Data

US 2018/0313844 A1    Nov. 1, 2018

Related U.S. Application Data

(60) Provisional application No. 62/491,239, filed on Apr. 27, 2017, provisional application No. 62/507,194, filed on May 16, 2017.

(51) Int. Cl.
*G01N 33/574* (2006.01)
*B01L 3/02* (2006.01)
(Continued)

(52) U.S. Cl.
CPC ...... *G01N 33/57492* (2013.01); *B01L 3/0241* (2013.01); *B01L 3/502761* (2013.01);
(Continued)

(58) Field of Classification Search
CPC ............. B01L 3/0241; B01L 3/502761; B01L 3/502784; G01N 21/6458; G01N 33/557;
(Continued)

(56) References Cited

U.S. PATENT DOCUMENTS

2006/0063160 A1    3/2006  West et al.
2010/0070191 A1    3/2010  Gold et al.
(Continued)

FOREIGN PATENT DOCUMENTS

WO    2008130623 A1    10/2008
WO    2009011808 A1    1/2009
(Continued)

OTHER PUBLICATIONS

Konry et al. (Scientific Report 2013 3: 3179; total 5 pages) (Year: 2013).*
(Continued)

*Primary Examiner* — Changhwa J Cheu
(74) *Attorney, Agent, or Firm* — Verrill Dana, LLP

(57) ABSTRACT

Bioassays are provided for detecting and analyzing responses from single cells and cell pairs suspended in micro-scale droplets (80-200 μm diameter) generated in microfluidic devices. Cell responses to various stimuli are analyzed. The stimuli are delivered by homotypic or heterotypic cells, small molecule drugs, and therapeutic agents including immunotherapeutics. The bioassays can be used to describe heterogeneity in any given cell population, and can be used in a clinical setting, such as profiling of patient-derived cells, designing personalized treatment strategies, and optimizing drug combinations for immunotherapy of tumors.

7 Claims, 4 Drawing Sheets

(51) Int. Cl.

| | |
|---|---|
| G01N 21/64 | (2006.01) |
| G01N 33/557 | (2006.01) |
| G01N 35/08 | (2006.01) |
| G01N 1/36 | (2006.01) |
| G01N 33/50 | (2006.01) |
| G01N 15/14 | (2006.01) |
| G01N 15/00 | (2006.01) |
| B01L 3/00 | (2006.01) |

(52) U.S. Cl.
CPC .......... *B01L 3/502784* (2013.01); *G01N 1/36* (2013.01); *G01N 21/6408* (2013.01); *G01N 21/6458* (2013.01); *G01N 33/5091* (2013.01); *G01N 33/557* (2013.01); *G01N 35/08* (2013.01); *B01L 2200/0647* (2013.01); *B01L 2200/0673* (2013.01); *B01L 2300/0816* (2013.01); *B01L 2400/0424* (2013.01); *G01N 15/147* (2013.01); *G01N 15/1484* (2013.01); *G01N 2015/008* (2013.01); *G01N 2015/1481* (2013.01); *G01N 2800/52* (2013.01); *G01N 2800/56* (2013.01); *G01N 2800/7028* (2013.01)

(58) Field of Classification Search
CPC ........... G01N 35/08; G01N 2800/7028; G01N 2800/56; G01N 2800/52
See application file for complete search history.

(56) References Cited

U.S. PATENT DOCUMENTS

| | | |
|---|---|---|
| 2013/0052648 A1 | 2/2013 | Yarmush et al. |
| 2013/0190196 A1 | 7/2013 | Onderdonk et al. |
| 2013/0260447 A1 | 10/2013 | Link |
| 2014/0158233 A1 | 6/2014 | Leslie et al. |
| 2015/0132837 A1 | 5/2015 | Frenz et al. |
| 2015/0346201 A1 | 12/2015 | Korny et al. |
| 2016/0177375 A1 | 6/2016 | Abate et al. |
| 2016/0231324 A1 | 8/2016 | Zhao et al. |
| 2016/0298173 A1 | 10/2016 | Wang et al. |
| 2017/0199173 A1 | 7/2017 | Konry et al. |
| 2018/0203005 A1 | 7/2018 | Konry et al. |

FOREIGN PATENT DOCUMENTS

| | | |
|---|---|---|
| WO | 2011112827 A2 | 9/2011 |
| WO | 2014028378 A2 | 2/2014 |
| WO | 2014107698 A1 | 7/2014 |
| WO | 2015031190 A1 | 3/2015 |
| WO | 2016011387 A1 | 1/2016 |
| WO | 2016059302 A1 | 4/2016 |
| WO | 2016100977 A1 | 6/2016 |
| WO | 2017027549 A1 | 2/2017 |
| WO | 2018013726 A1 | 1/2018 |
| WO | 2018081478 A1 | 5/2018 |
| WO | 2017011819 A1 | 1/2019 |

OTHER PUBLICATIONS

Lee et al. (Clin. Cancer Res. 2012 18: 2781-2790) (Year: 2012).*

Konry, T., et al., "Live single cell functional phenotyping in droplet nano-liter reactors", Scientific Reports, 3, 3179(2013). https://doi.org/10.1038/srep03179.

Lee, D. W., et al., "The Future is Now: Chimeric Antigen Receptors as New Targeted Therapies for Childhood Cancer", Clinical Cancer Research, 2012;18(10):2780-2790. doi:10.1158/1078-0432.CCR-11-1920.

Chiu, Yu-Jui et al., "A single-cell asay for time lapse studies of exosome secretion and cell behaviors", Small, Jul. 2016; 12(27): 3658-3666. doi: 10.1002/smll.201600725.

Huang, T. et al., "Current Progresses of Exosomes as Cancer Diagnostic and Prognostic Biomarkers", International Journal of Biological Sciences, 2019; 15(1): 1-11. doi: 10.7150/ijbs.27796.

Konry, T. et al., "Ultrasensitive Detection of Low-Abundance Surface-Marker Protein using Isothermal Rolling Circle Amplification in Microfluidic Nano-Liter Platform", Small Feb. 7, 2011; 7(3): doi: 10.1002/smll.201001620.

Li, A. et al., "Exosomal proteins as potential markers of tumor diagnosis", Journal of Hematology & Oncology, 2017, 10:175, DOI: 10.1186/s13045-017-0542-8.

Son KJ, et al., "Microfluidic compartments with sensing microbeads for dynamic monitoring of cytokine and exosome release from single cells", Analyst. 2016;141(2):679-688. doi:10.1039/c5an01648g.

Verweij, F. et al., "Quantifying exosome secretion from single cells reveals a modulatory role for GPCR signaling", Journal of Cell Biology, 2018, vol. 217, No. 3, 1129-1142, doi: 10.1083/jcb.201703206.

Zhu, L. et al., "Exosomes Derived from Natural Killer Cells Exert Therapeutic Effect in Melanoma", Theranostics, 2017, vol. 7, Issue 10, 2732-2745. doi: 10.7150/thno.187752.

Sato, K., "Microdevice in Cellular Pathology: Microfluidic Platforms for Fluorescence in situ Hybridization and Analysis of Circulating Tumor Cells", Analytical Sciences, Sep. 2015, vol. 31, 2015, The Japan Society for Analytical Chemistry.

Liu, Y. et al., "Development of single-cell array for large-scale DNA fluorescence in situ hybridization", Lab Chip, Apr. 7, 2013; 13(7): pp. 1-18 doi: 10.1039/c21c40364a.

Tai, CH, et al., "A novel integrated microfluidic platform to perform fluorescence in situ hybridization for chromosomal analysis", Microfluid Nanofluid (2013) 15: 745-752 doi: 10.1007/s10404-13/1190-0.

Cohen, N. et al., "Approaching near real-time biosensing: Microfluidic microsphere based biosensor for real-time analyte detection", Biosensors and Bioelectronics, Apr. 2015, vol. 15, No. 66, pp. 454-460.

Goldberg, A. et al., "Cloud-Enabled Microscopy and Droplet Microfluidic Platform for Specific Detection of *Escherichia coli* in Water", PLoS One, Jan. 27, 2014, vol. 9, No. 1, pp. 1-9 doi: 10.1371/journal.pone.0086341.

Lagus, T. et al., "High-throughput co-encapsulation of self-ordered cell trains: cell pair interactions in microdroplets", RSC Advances, Aug. 21, 2013 (Aug. 21, 2013), vol. 3, No. 43, pp. 20512-20522 doi: 10.1039/c3ra43624a.

* cited by examiner

LIVE SINGLE-CELL BIOASSAY IN MICRODROPLETS

CROSS REFERENCE TO RELATED APPLICATIONS

This application claims the priority of U.S. Provisional Application No. 62/491,239, filed 27 Apr. 2017 and entitled "Live Single-Cell Bioassay in Micro-Droplets", and of U.S. Provisional Application No. 62/507,194, filed 16 May 2017 and entitled "Live Single-Cell Bioassay in Micro-Droplets". Both of said provisional applications are hereby incorporated by reference in their entireties.

BACKGROUND

Microfluidic droplets compartmentalize cells and cell-secreted products within picoliter volume emulsions, thereby limiting communication between nearest neighbors while allowing interaction between the co-encapsulated cells. These nanoliter droplets serve as bioreactors for the encapsulated cells and allow appropriate gas exchange necessary to ensure cell viability and functionality. Droplets have been used previously to entrap mammalian and microbial cells and assess responses at the single cell level.

Systemic cellular responses are a summation of individual responses of thousands of single cells, which are known to be intrinsically heterogeneous (1,2). Cell heterogeneity has been assessed at single cell level by evaluating variations in genotypic and phenotypic traits using a number of bioanalytical platforms (3,4,5,6). Microfluidic single cell analysis has been used to reveal cellular heterogeneity in certain cell types (7). A major advantage of microfluidic phenotypic profiling is that it allows time resolution of dynamic, transient events mediated by single cells as well as cell-cell interactions (8).

Transient cell-cell interactions have been detected in various cell types and developmental processes, for example, in neural cells during axon guidance, in epithelial-fibroblast contact during cell migration, and in immune cell interactions (9,10). One example of rapid and transient cellular interaction is exhibited by natural killer (NK) cells, which form fast-acting synapses with heterotypic cells over a matter of minutes (11). NK cells are components of the innate immune system, which mediates effector functions directly after identifying stress-related molecular signals and foreign bodies. NK cells elicit fast contact-dependent cytotoxicity and slow receptor-mediated apoptosis in target cells, and also engage in co-stimulatory signaling and bidirectional cross talk with other immune cell types (11). NK cells are further known to secrete soluble cues, including cytokines, which lead to activation of adaptive immunity (12). However, the central role of NK effector function is mediated via immunological synapses at cellular interfaces. NK synapses can be activating (lytic), inhibitory, or regulatory, depending on the prevalence of activating or inhibitory receptors at the synapse (11,13,14). Activating, or lytic, synapses lead to the restructuring of the actin cytoskeleton, polarization of lytic granules containing perforin and associated cytotoxic molecules at the synapse, and targeted secretion of granules onto the target cell to promote cytolysis (15,16). The lifetime of activating synapses is longer than that of inhibitory synapses, and it has been hypothesized that the duration of synaptic contact is a key factor in regulating downstream effector function (17). Thus, the efficiency of NK cytotoxicity can be modified by mechanisms that enhance or decrease the intercellular synaptic contact periods.

Individual NK cells are highly heterogeneous with respect to the expression of activating receptors (17). This suggests that there are heterogeneities in activation and functional responses of NK cells at the single cell level, which affect immune responses at the population level. While flow cytometry allows quantitative phenotypic assessment of NK cells, dynamic analysis of single cell responses over long time periods is better achieved by time-lapse microscopy. A few studies have assessed interaction of target cells with activated or resting NK cells at single cell resolution (18, 19,20); the results demonstrate significant differences in NK cell cytotoxic capacity, migratory behavior and phases of interaction.

NK cells have been shown to possess anticancer activity, but this effect is suppressed in patients with advanced disease. One of the mechanisms of NK inhibition is the checkpoint inhibitor programmed death 1 (PD-1) and its ligands (PD-L1 and PD-L2). The binding of its ligands to PD-1 on immune cells induces a state of effector cell exhaustion associated with immune tolerance and loss of immune activation. PD-L1 is known to be expressed in a number of human malignancies and promotes tumor growth as well as escape from cytotoxic T lymphocyte-mediated cell lysis (21,22). Regulation of lymphocyte function via the PD-1/PD-L1 pathway varies due to intra-patient and inter-patient heterogeneity in expression of these markers (23).

There is a need to characterize functional heterogeneity in NK cell responses in the presence of PD-L1 inhibitors, so as to more effectively carry out immunotherapy.

SUMMARY

The present technology embodies a number of bioassays that focus on heterotypic cell-cell interactions in microfluidic droplets. The droplets utilize co-encapsulation of small numbers of cells of one or more cell types at varying ratios, allowing analysis of single and multiple cell responses in a single experiment. The technology further provides the flexibility of tracking singular as well as serial interactions between two cell types, thereby mimicking the situation in vivo where one cell type encounters populations of secondary cell types. The droplet-based platform can be used to perform the following: 1) live cell functional phenotyping based on both surface and secretion markers; 2) quantification of functional responses of activated effector immune cells dynamically in the context of anti-tumor immunity; 3) analysis of the effect of immune checkpoint blockade agents; 4) cytotolytic immune cell-mediated target cell killing; and 5) analyzing acquired resistance to chemotherapeutic and immunotherapeutic drugs used for cancer treatment.

The technology can also be summarized with the following listing of embodiments.

1. A method of analyzing a cell-cell interaction, the method comprising the steps of:
   (a) providing a microfluidic device capable of forming aqueous microdroplets in oil, the device comprising a translucent microdroplet array chamber, and providing an imaging microscope;
   (b) preparing a plurality of aqueous microdroplets in oil using the microfluidic device, each microdroplet comprising two or more individual cells in suspension and optionally one or more reagents for analyzing an interaction between said cells;

(c) directing the plurality of aqueous microdroplets into the microdroplet array chamber;

(d) obtaining a series of images of the microdroplet array chamber over a period of time using the imaging microscope; and (e) analyzing a cell-cell interaction using said images.

2. The method of embodiment 1, wherein individual microdroplets comprise two or more different types of cells whose interaction is analyzed.
3. The method of embodiment 2, wherein the microdroplets prepared in (b) comprise two or more reagents that are capable of specifically labeling each of said two or more different types of cells.
4. The method of embodiment 2, wherein individual microdroplets comprise one or more NK cells and one or more tumor cells, and killing of the tumor cells by the NK cells in analyzed.
5. The method of embodiment 4, wherein the microdroplets prepared in (b) comprise a reagent capable of indicating different optical signals for live cells and dead cells.
6. The method of embodiment 4, wherein the microdroplets comprise a checkpoint inhibitor.
7. The method of embodiment 6, wherein the checkpoint inhibitor is an anti-PD-L1 antibody.
8. The method of embodiment 4, wherein cell-cell interactions are analyzed using an agent based model.
9. The method of embodiment 2, wherein individual microdroplets comprise dendritic cells, T cells, and tumor cells.
10. The method of embodiment 9, wherein the dendritic cells have been pre-incubated with one or more antigens from said tumor cells.
11. The method of embodiment 9, wherein the dendritic cells derive from a dendritic cell vaccine.
12. The method of embodiment 10, wherein the T cells and tumor cells both are obtained from a patient.
13. The method of embodiment 2, wherein individual microdroplets comprise T cells and tumor cells.
14. The method of embodiment 13, wherein the T cells are CAR T cells comprising a chimeric antigen receptor that is suspected of recognizing an antigen on the tumor cells.
15. The method of embodiment 1, wherein the analysis of cell-cell interactions is used to modify a patient therapy.

DETAILED DESCRIPTION

Figures 1A, 1B, 1C, 1D, 1E, 1F, 1G:
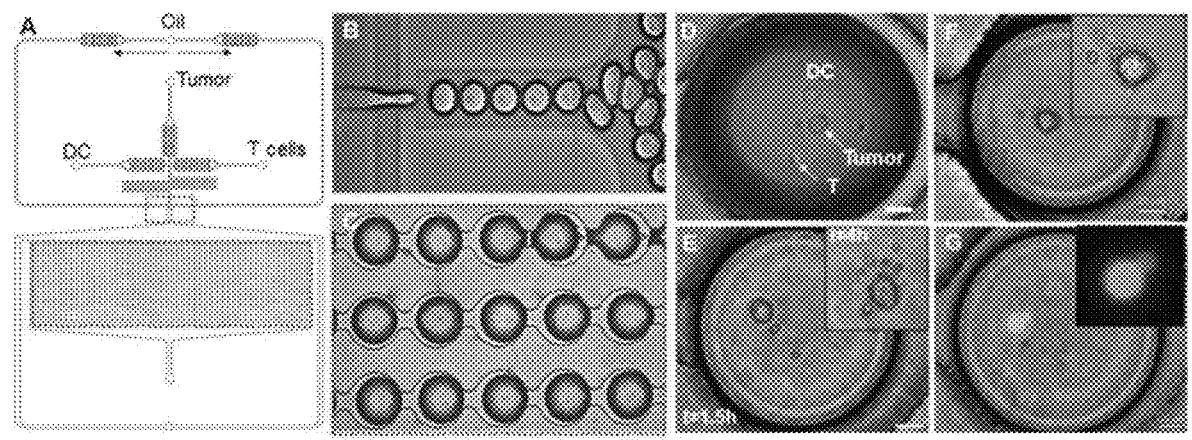
FIGS. 1A-1G show the results of an experiment co-encapsulating dendritic cells, T cells, and tumor cells. (1A) Schematic diagram of integrated three-inlet droplet generation and microarray device. (1B) Generation of nanoliter droplets. (1C) Droplets loaded in microarray for stable docking. (1D) Co-encapsulation of three types of cells in droplets. (1E) Cellular exocytosis observed in droplet. Inset: Magnified image of vesicles secreted by DC at 4 hours. (1F) Morphology of single DC and T cell in droplet. Inset: Magnified image of dendrite extension by DC. (1G) Blebbing of cell membrane prior to cell death. Inset: Fluorescent image of cell (labeled with calcein-AM) membrane deformation. Scale bar: 20 p.m.

The present technology utilizes an integrated microfluidic droplet array platform to analyze interactions between cells at the single cell level. The platform is useful for characterization of natural killer (NK) cell-mediated cytotoxicity against tumor cells and the effectiveness of dendritic cell vaccines. The technology also can be used to evaluate the heterogeneity of cell populations with respect to their interactions with other cells, such as to evaluate the potency of an individual patient's immune response against cancer cells of the patient, and to follow the progress of such responses before, during, and after treatment, such as immunotherapy.

Characterization of the heterogeneity in immune reactions requires assessing dynamic single cell responses as well as interactions between the various subsets of immune cell subsets. However, there are few methods available that allow dynamic investigation of immune cell interactions, and other types of interactions among freely dispersed cells, without physically constraining the non-adherent cells. The microfluidic droplet microarray platform of the present technology permits rapid functional analysis of single cell responses and co-encapsulation of heterotypic cell pairs, thereby making possible the evaluation of the dynamic activation state of primary T cells, and other cellular functions and phenotypes.

NK cell dysfunction occurs in patients with cancer, such as advanced myeloma, due to altered expression of immunomodulatory cytokines and inhibitory receptor—ligand signaling. NK cells are heterogeneous and form short-lived, fast-acting synapses with target cells. In an embodiment of the present methods, pairs of NK cells and target cell are co-encapsulated in sub-nanoliter droplets to dynamically monitor intercellular interaction and effector outcomes at the single cell level. NK cells depict potent cytolytic activity against target cells, such as myeloma cells, but also show marked heterogeneity in immune complex duration, lytic death, and mechanism of interaction. Pre-treatment of target cells with immune checkpoint inhibitors such as anti-PD-L1 antibody introduces further heterogeneity in contact-dependent interactions, with increased numbers of cells forming shorter conjugation and requiring multiple interactions before target death. Based on the experimental findings, a single-cell agent-based model incorporating PD-1 and PD-L1 receptors was developed to simulate varying disease states and predict the efficacy of NK-mediated target cell death in the presence of drugs targeting this pathway. The model is also useful for studying the interaction of genetically modified NK cells for adaptive immunotherapy.

To investigate NK cell interaction with cancer cells, the present technology utilizes an integrated microfluidic droplet generation/docking platform. This approach combines the advantages of microscopic analysis at sub-cellular resolution with spatiotemporal evaluation of individual cell pairs. The dimensions of microwells can be adjusted to be compatible with that of the assayed cells to optimize single vs. multiple cell loading. Also, in contrast to other microwell-based platforms that require sequential cell loading steps, which increases the possibility of cell drifting if the cells are non-adherent, the present droplet microfluidic approach loads heterotypic cell pairs into the device in a single step. Isolation of cells in droplets minimizes crosstalk with neighboring cell pairs while allowing manipulation of encapsulated cells. This is not possible in open configuration hydrodynamic trap arrays. NK cells secrete a number of cytokines including MIP-1β and IFN-γ, and NK cell-to-cell communication regulates cell function and cytokine responsiveness (18, 28). Compartmentalizing individual NK cell-target cell pairs within droplets decouples homotypic signaling from heterotypic effector function. Cell-secreted factors are retained within the picoliter volume droplets, permitting contact-dependent as well as paracrine signaling between NK and target cells. Furthermore, droplets allow characterization of suspension cells, such as cells of hematologic origin, for long periods without physical restraints (e.g., traps, weirs) or adhesive ligands (e.g., antibodies). This makes the platform suitable for investigating both stable and discontinuous interactions between cells of various immune subsets including T cells, dendritic cells, and NK cells.

The inventors have quantified heterogeneous profiles of NK cell conjugation with myeloma cells and subsequent myeloma cell death. They observed fast as well as slow target cell lysis mediated by contact-dependent methods at a 1:1 cell ratio. Single NK cells were also capable of simultaneously interacting with and killing up to four target cells. NK-mediated target death was characterized in the presence of an anti-PD-L1 blocking antibody. Humanized antibodies against PD-1 and PD-L1 are presently utilized in clinical trials and have shown great promise in antitumor immunotherapeutic treatments (29,30). In droplets, greater variability was observed in dynamic interaction parameters in the presence of anti-PD-L1 antibody. The experimental results were used to develop an agent-based model of single NK cell lytic interaction with a target cell. Incorporating the expression of PD-1/PD-L1 molecules in this model, progressive disease states can be simulated, such as disease states characterized by increased levels of PD-1 and PD-L1, and treatment of such disease states by inhibition of the pathway with anti-PD-1 drugs also can be simulated.

The microfluidic device and methods of the present technology, through their ability to isolate and maintain single cells, pairs of cells, or small groups of three or more cells, make it possible to analyze various cell phenotypes and cell-cell interactions. These include, but are not limited to, cell viability, susceptibility of tumor cells to an antitumor agent, activation of an immune response (such as activation of T lymphocytes, B lymphocytes, dendritic cells, or other immune system cells), the effectiveness of a cellular vaccine (such as a dendritic cell vaccine), the presence or absence of a biomarker, and the action of a pharmaceutical agent on a target cell or non-target cell of interest (i.e., generation of dose-response curves or the determination of inhibition constants or binding or dissociation constants, or the observation of cellular level signal transduction events related to the mechanism of action of a drug or a side effect of a drug). The ability to study the responsiveness of a patient's own immune cells against a tumor of the patient is of particular importance. This can be useful to evaluate the effectiveness of a cellular vaccine. The cancer can be, for example, a solid tumor, liquid tumor, hematologic tumor, renal cell cancer, melanoma, breast cancer, prostate cancer, testicular cancer, bladder cancer, ovarian cancer, cervical cancer, stomach cancer, esophageal cancer, pancreatic cancer, lung cancer, neuroblastoma, glioblastoma, retinoblastoma, leukemia, myeloma, lymphoma, hepatoma, adenoma, sarcoma, carcinoma, blastoma, cancer of the colon, lung, kidney, liver, endometrium, cervix, ovary, thyroid, skin, or central nervous system. Several specific uses for cell phenotype assays are summarized in the examples below.

The microfluidic chips disclosed herein are designed with variations on geometry to co-encapsulate small numbers of cells, such as two cells, three cells, four cells, five cells, or up to 10 cells, optionally combined with culture medium, assay reagents, and drug candidates. A polydimethylsiloxane (PDMS) chip cam be generated using standard soft lithography methods, combining functionalities of droplet generation and an incubation chamber array of up to 1000 droplets. The generation of monodisperse droplets is conducted in a microchannel through shearing flow at a flow-focusing zone. Either two or three perpendicular inlet channels form a nozzle. Individual syringe pumps are used to control flow rates of the central stream of the oil phase and the stream of cells and bioassay reagents (e.g., microsphere sensors and/or detection antibodies). The channels are coated with Aquapel (PPG Industries), and the flow rates are controlled by syringe pumps (Harvard Apparatus). To form droplets, the flow rate ratio of water to oil may be adjusted to the Qw/Qo=0.5 (Qw=1 μL/min and Qo=2 μL/min). The generated droplet volume can be, for example, ~1.8 nL corresponding to a spherical droplet diameter of 150 μm.

Once initial functional determinations are made with a system that can be rapidly re-configured as necessary for optimization and at relatively low cost, a mechanically more robust PDMS/glass chip may be used that has the requisite characteristics for inclusion in a diagnostic device. The chip also may be composed of both robust glass for droplet generation and gas permeable PDMS incubation for cell interrogation in droplets. This microdroplet system enables rapid droplet generation to produce as many as 10,000 monodispersed droplets per second ranging from 5 μm to 250 μm in diameter each. The flow rates in the device may be controlled by Mitos pressure pumps that provide a pulseless liquid flow which is ideal for applications where a highly stable flow is required, such as droplet formation. In this device, cells and optional reagents or media are co-encapsulated in droplets that are formed at a T-junction. The droplets then enter the PDMS incubation part of the chip. To generate the PDMS part of the device, the PDMS layer may be bonded to the glass chip with serpentine geometry for cell incubation. This PDMS based incubation part of the chip allows appropriate gas exchange to maintain live co-encapsulated mammalian cells, such as human cells, in microreactor droplets during interrogation. Details of suitable microfluidic devices and methods of using them for co-encapsulation of cells in aqueous droplets in an oil stream can be found in WO2017/011819, which is hereby incorporated by reference.

In order to image cells by fluorescence, up to 3 solid-state diode lasers (e.g., Crystalaser Inc.) may be focused in slits across the microfluidic channel corresponding to the excitation wavelengths of the three fluorophores (405 nm, 488 nm and 633 nm). In combination with the fluorescence detection filters, these are selected to be well spectrally separated to allow multiplexed detection. A set of 3 PMTs may be used to detect the fluorescent signal from labeled droplets. Fluorescent light may be collected with a second 60+ microscope objective, split into 3 detection channels with 50-50 beam-splitters, and then filtered with appropriate band-pass filters corresponding to each fluorophore (centered at: 450 nm, 550 nm, and 680 nm). The output of each PMT may be pre-amplified and then acquired with a multifunction data acquisition board (National Instruments) connected to a personal computer. Software running on the PC allows real-time detection of fluorescent spikes on each of the 3 detector channels. That the laser and filter combinations can be adjusted to allow flexible operation with other fluorophores as needed.

After passing through the laser slits, droplets may be diverted into collection outlets using dielectrophoresis and a sorting junction. A micro-electrode may be deposited next to the channel at the sorting junction during fabricated and connected to a high voltage, programmable power supply (Stanford Research Systems). Software written in Matlab may be used to control the magnitude of and frequency the applied AC voltage applied across the electrode on the basis of droplet fluorescent signature, thereby controlling the magnitude of deflection and outlet channel. The amplitude of the AC potential may be selected to be as small as possible to minimize the possibility of shearing the droplets.

A white-light source and monochrome CCD camera may be employed to allow alignment of the microfluidic chip on the subsystem, and in particular to align orthogonal illumination of the flow channel with the 3 laser slits and detection optics.

Immunological synapse formation was investigated between T cells and DCs pre-exposed to cancer cell lysate. The activated T cells then mediated the death of co-encapsulated cancer cells. The rapid reaction kinetics in droplet microfluidics facilitated cell-cell interaction and delivery of cytotoxic hits to cancer cells within two hours in this integrated platform. The microfluidic droplets also allowed determination of strong heterogeneity during immune synapse formation with respect to transient vs. stable interactions and the duration of T-DC conjugate formation. Serial brief encounters were observed between the same DC-T cell pair, which would not be possible with microwells or hydrodynamic cell traps. Further detected were contact dependent cancer cell lysis by NK cells, and quantified heterogeneous profiles of cell conjugation, delivery of lytic hits and target death. It was observed that a single NK cell resulted in multiple cell deaths, sometimes interacting with up to four target cells simultaneously. NK-mediated target cell lysis in the presence of anti-PD-L1 blocking antibody was also characterized, as the PD-1/PD-L1 axis is involved in promoting immune escape in a number of solid and liquid tumors. Humanized antibodies against PD-1 and PD-L1 are presently utilized in clinical trials and have shown great promise in antitumor immunotherapeutic treatments. In droplets, 50% single target cell lysis was observed in significantly shorter duration compared to control. Taken together, the data suggest that this integrated droplet-based microfluidic platform provides an important tool for dynamic real-time analysis of synaptic communications and downstream effector functions of immune cells.

The microfluidic device was similar to that described above. The droplet generation junction was followed by a large docking array consisting of 1000 trapping sites where the droplets were stably arrested. Consistent droplet sizes of ~100 μm diameter (i.e., 520 pL volume) were obtained by optimization of the flow rates of the two phases (FIG. 10C). The cell encapsulated droplets were maintained for up to 48 hours in a $CO_2$-rich and humidified atmosphere, and minimal droplet shrinkage was observed. By coordinating individual inlet flow rates and optimizing initial cell density, large numbers of droplets were routinely obtained with co-encapsulation of all three types of individual cells.

Several types of cell co-encapsulation were performed using this approach: T-DC interaction, TDC-cancer cell interaction and NK-cancer cell interaction, unstimulated T cells derived from the non-adherent fraction of peripheral blood mononuclear cells, and mature DCs generated from adherent mononuclear cells cultured with cytokines were added through separate inlets to ensure that cell pairing and subsequent activation occurred only in the droplets. Likewise, NK cells and cancer cells (RPMI-8226 cells, a multiple myeloma line) were co-encapsulated in droplets by flowing through separate fluid inlets, thus allowing the investigators to monitor the early signaling events and synapse formation in this platform. For these studies with two cell types, the third inlet was used to perfuse media only. Since droplets provide a culture platform highly compatible with non-adherent cells, it was possible to observe a number of morphological features of the encapsulated cells, including secretory vesicle formation, dendrite extension by DCs, and membrane blebbing prior to cell death. The results showed both continuous and intermittent interactions between cell pairs, leading to quantitative analysis of dynamic parameters corresponding to these interactions. In addition, all cellular secretions remained undiluted within the droplets, leading to noncontact-mediated activation of co-encapsulated cells while minimizing stimulation of neighboring cells.

The present technology includes methods for modeling NK cell contact dynamics. Various mathematical models have been developed to analyze and model the immune system. Traditionally, ordinary differential equations (ODEs) are used for modeling population dynamics, for example, delay differential equations (DDEs) and stochastic differential equations (SDEs). In certain cases, spatial effects are also important and cannot be ignored. Partial differential equations (PDEs) have been used to explicitly model the spatial dependence. However, such differential equation-based models are obviously not suitable for single cell studies of individual cell behaviors and interactions rather than averages of population dynamics. Therefore, the present model is based on the so-called agent-based model (ABM) paradigm, which is more intuitive and suitable for modeling individuals (agents) and their interactions with other individuals and environment. Heterogeneity and stochasticity are easily added into the ABM. Compared to standard ABMs, which usually model many agents (cells) and their interactions (which are usually modeled by a complex network), the present model considers only two cells and their interactions. Such a simple setting allows focus on the status of the individuals in a more dynamic way. The model incorporates the details of the complex interactions between NK cells and cancer cells directly and how their status changes according to the different stages of their interactions with or without the PD-1/PDL1 pathway.

To model the single-cell interaction, the ABM was coupled with a Monte Carlo simulation, averaging the results over several interactions. The entire model can be implemented using MATLAB.

Model with no PD-1/PD-L1 Components

To start, we assume that there are two cells confined within the droplet, described as a circle with radius 150 pm. The NK cell is modeled as a circular cell with radius 31 μm and the cancer cell is similarly modeled as a circle with radius 6 μm. These sizes were taken from experimental estimates of cell sizes size. In the droplet experiments, the initial positions and distances between the centers of the two cells are placed at random. Thus, we take the mean and standard deviation of the logarithm of these initial distances to create a normal distribution, from which we can draw for each simulation. Thus, we choose the distances from a distribution defined as:

$$d_i = e^{(\sigma x + \mu)} \quad (1)$$

where $d_i$ is the initial distance between the NK cell and the cancer cell, cr and μ are the standard deviation (0.62) and mean (3.48) of the logarithm of initial distances across the experiments, and x is a random number, normally distributed between 0 and 1. This approach guarantees that the distances are positive, described on a Cartesian grid, then, we assume the droplet is within the circle $x^2+y^2=150$, the NK cell is located at $$\left(-\frac{d_i}{2}, 0\right),$$

and the cancer cell is located at $$\left(\frac{d_i}{2}, 0\right),$$

where all units are in Jana.

At first, we assume that the two cells move under Brownian motion with drift. In other words, the two cells are allowed to perform a random walk, before any interaction occurs. To compute the diffusion coefficients, we take the average "speed" of the cells computed from the experimental data. Over a certain time interval, a picture of the cells is taken and their locations noted. From this an average speed of the cells is computed. From this we obtain the diffusion coefficient, $$D = \frac{v_{avg}^2 \Delta t}{4}.$$

For this particular simulation, we assume there is no drift (i.e., the cells do not generally track each other). However, in general this is easily included in the model if, for instance, the NK cell were to track the cancer cell once it is detected.

The movements of the cells are simulated over a fixed time frame, T, with a time step size of 0.1 minutes. For each time step, the positions of the cells are updated based on this motion:

$$x(t_i) = x(t_{i-1}) + \sqrt{4D\Delta t}\beta + \alpha x_d \Delta t,$$

$$y(t_i) = y(t_{i-1}) + \sqrt{4D\Delta t}\beta + \alpha y_d \Delta t,$$

where ti is the time at step i, D is the diffusion coefficient (different for the cancer and NK cells). At is the time step size (0.1 minutes), $\beta$ is a uniformly distributed random number between 0 and 1, a is the drift coefficient, and $x_d$ and $y_d$ are the x and y distances between the cells at the given time step. Note that if the cells are close to the boundary, this type of motion might move it outside of the droplet. To correct for this, if the random motion moves outside, we just assume the cell stays on the boundary for that step. A similar procedure is done, to make sure that the cells do not overlap, and only touch.

For the first set of simulations, we assume no PD-1/PD-L1 components. The NK and cancer cells move under Brownian motion as described above. Once they get within a certain contact radius, $r_e$, we assume that the NK cell is close enough to perform a lytic hit. Then, based on the experimental data (mean=4.13 min, stdev=0.984 min), we compute the average time it takes the cancer cell to die once the lytic hit is performed. Similar to the calculation to get the initial distance between the cells, we compute a uniformly distributed random number for each simulation. These simulations are performed 2000 times in a Monte Carlo approach, with fixed timestepping (T, $\Delta t$=0.1), cell and droplet radii, contact distance ($r_e$), and diffusion coefficients (D=0.13253 for NK cells and D=0.09024 for cancer cells). As described above the initial cell distances and killing times, and motion of cells are drawn from a random distribution based on experimental data and Brownian motion, respectively.

Model with PD-1/PD-L1 and Variation in Drug Efficiency

In the second set of experiments, we now assume that the cancer and NK cells may have PD-1/PD-L1 components. Additionally, a drug may be present that inhibits the functionality of these receptors. In the absence of the drug, and with both cells having the appropriate receptors, the NK cell will not kill the cancer cell in any amount of time. For each simulation, we draw a random number for the NK cell and the cancer cell to see if they contain the PD-1/PD-L1 receptors. We vary this parameter to obtain different averages of the likelihood of the individual cells having the receptors.

To simulate the drug, we also assume varying probabilities of the effectiveness of the drug. If in the given simulation the drug is deemed effective, the PD-1/PD-L1 receptors are ignored and the simulation is performed as in the no PD-1/PD-L1 case. If it is not deemed effective, then the NK cell cannot kill the cancer cell if the receptors are present.

EXAMPLES

Example 1

General Methods

Microfluidic Device Fabrication and Droplet Generation

The microfluidic devices were fabricated in accordance with standard soft-lithography protocols. The device interior was made hydrophobic by injecting AQUAPEL glass treatment (Aquapel, Pittsburg, USA) for 15 minutes immediately prior to experiments, followed by flushing with air. The device included three inlets and two outlets. Each inlet was connected to individual syringes containing aqueous (i.e., cell suspension in media) or oil-based fluids. The syringes were operated by individual syringe pumps (Harvard Apparatus, USA). The oil to aqueous flow rates were generally maintained at a ratio of 4:1 to obtain optimal droplet sizes. The oil phase consisted of FLOURINERT FC-40 (Sigma, St. Louis, Mo.) supplemented with 2% w|w surfactant (008-FLUOROSURFACTANT, Ran Biotechnologies, Beverly, Mass.).

Cell Isolation and Culture

RPMI-8226 (multiple myeloma cell line) was purchased from American Type Culture Collection (ATCC, Manassas, Va.) and maintained in RPMI-1640 medium supplemented with 10% fetal bovine serum and 1% antibiotic-antimycotic solution (Corning Cellgro, Manassas, Va.). All cells were grown at 37° C. under 5% $CO_2$ in a humidified atmosphere. Cells were routinely passaged every three days and harvested at a density of $1\times10^6$ viable cells $mL^{-1}$.

The isolated mature dendritic cells and naive T cells were prepared as follows. Peripheral blood mononuclear cells (PBMCs) were isolated via Ficoll density gradient centrifugation from whole blood obtained from buffy coats. RPMI 1640 complete medium was prepared using heat inactivated 10% human AB male serum (Sigma, St. Louis, Mo.), 100 U mL1 penicillin and 100 ug mL-I streptomycin (Mediatech, Herndon, Va.), and 2 mM L-glutamine (Mediatech). PBMCs were incubated in this RPMI complete medium for 1 hour at 37° C. The non-adherent T cell-rich population was removed by aspiration and cryopreserved. The adherent fraction was cultured with granulocyte-macrophage colony-stimulating factor (GM-CSF, 1000 U $mL^{-1}$, Berlex, Wayne/Montville, N.J.) and interleukin-4 (IL-4, 1000 U $mL^{-1}$, R&D Systems, Minneapolis, Minn.)) supplemented complete medium for a period of 5 days to differentiate into immature DC populations. The DCs were further matured by treating them with 25 ng $mL^{-1}$ TNFa for an additional 2 days. Expression of DC costimulatory and maturation markers (CD86 and/or CD83) was assessed by flow cytometric analysis.

Primary human NK cells were sorted via FACS from peripheral blood of healthy donors by labeling PBMCs with FITC-conjugated CD56 antibody (BD Biosciences, San Jose, Calif.). Freshly isolated cells were maintained in RPMI-1640 media containing 10% FBS, 1% antibiotic and 100 U $mL^{-1}$ IL-2 (Roche Diagnostics, Indiapolis, Ind.).

Cell Viability Studies

Cell viability in droplets was determined by incorporating the LIVE/DEAD viability/cytotoxicity assay reagents in droplets (Life Technologies, Carlsbad, Calif.). The final concentration of calcein AM (live cell indicator) and ethidium homodimer-1 (EthD-1, dead cell indicator) was maintained at 2 µM and 4 µM respectively. Calcein AM was detected by time-lapse microscopy at excitation/emission: 494/517 nm. EthD-1 was read at 528/617 nm. The proportion of live cells was calculated as a ratio of the number of live cells to the total number of cells as expressed as percentage viability.

Differential Cell Labeling

Co-encapsulation studies were performed by labeling different cell types with fluorescent trackers including CFSE Cell Trace and CellTracker Red CMTPX according to manufacturer's instructions Life Technologies (Grand Island, N.Y.). Briefly, CFSE stock solutions (5 mM) were prepared in dimethyl sulfoxide (DMSO) and used at a final concentration of 10 11M by diluting in 1× phosphate buffered saline (PBS). The cells were labeled for 15 minutes at 37° C. on a shaker (300 RPM). Excess labeling solution was removed by aspiration and the cells suspended in fresh growth media before use. Dye uptake was visualized using the FITC filter (Ex/Em=492/517 nm). CMTPX dye stocks were prepared at a concentration of 10 mM and used at a final concentration of 10 μM. The cells were labeled 45 minutes at 37° C. and visualized using a DsRed filter (Ex/Em=577/602 nm). Cell nuclei were labeled with Hoechst at room temperature for 10 minutes. DC activation and cell-cell interaction in droplets: Dendritic cells (DCs) were stimulated with 100 μg mL$^{-1}$ ovalbumin (OVA (323-339)) peptide conjugated with FITC (Anaspec, Fremont, Calif.) overnight.1341 The Ag-loaded DCs were washed twice to remove excess OVA-FITC from the solution prior to treatment with CCL21 for 2 hours (25 ng mL$^{-1}$, Abcam Cambridge, Mass.). Untreated T cells were labeled with CMTPX tracker off-chip. To promote single cell encapsulation in droplets, all experiments were performed by incubating 1×10$^6$ cells mL$^{-1}$ of each cell type through distinct inlets of the microfluidic platform. Control experiments were performed with untreated DCs and T cells suspended in complete growth media in the droplets. In experiments utilizing RPMI-8226 cells, the third cell type was labeled only with Hoechst to distinguish it from the other cells.

Generation of DC-Based Vaccine Cells (a) DC/MM fusion cells: DC/MM (multiple myeloma) fusion cells were generated by mixing DCs with RPMI-8226 cells at a ratio of 1:1 and washed 3 times with serum-free RPMI 1640 complete growth medium. The cell pellet was resuspended in 1 mL of 50% polyethylene glycol (PEG) solution for 2 minutes at room temperature. The PEG solution was progressively diluted and the cells were washed twice with serum free medium. The DC/MM fusion cells were cultured in RPMI complete medium in the presence of GM-CSF. The fusion cells were identified by determining the percentage of cells expressing unique DC and tumor antigens by immunocytochemical analysis. (b) DCs pulsed with tumor lysate: I×10$^6$ RPMI-8226 tumor cells were washed in RPMI-1640 media and suspended in 1 mL medium. Tumor lysate was then prepared by sonicating the cells for several seconds as per standard protocol. DCs were generated from healthy donors as discussed above. Following TNF-a-induced maturation (25 ng mL$^{-1}$ for 48 hours), DCs were pulsed with 200 μg mL$^{-1}$ tumor lysate for 5 days. Un-pulsed DCs were used as a control.

Activation of NIC Cells and NK Mediated Cytolysis

CD56+ NK cells were labeled with Hoechst nuclear dye for 10 minutes prior to incubation in droplets. Prior to PD-L1 blockade experiments, RPMI-8226 cells were pre-treated with 500 μg mL$^{-1}$ interferon gamma (IFN-y, R&D Systems) for 24 hours 1201 and subsequently incubated with anti-PD-L1 blocking antibody (BPS Bioscience, San Diego, Calif.) for 24 hours. The treated cells were washed, labeled with calcein AM and Hoechst off-chip for 30 minutes at 37° C. at the above-mentioned concentration and co-encapsulated with NK cells in droplets.

Image Acquisition, Processing and Statistical Analysis

The phase/fluorescent images of cells in droplets were captured using Zeiss Axio Observer Z1 microscope (Zeiss, Germany) equipped with a Hamamatsu digital camera CI0600 Orca-R2, 10-40× objectives and standard FITC/DAPI/TRITC filters. The microfluidic device containing cells co-encapsulated in droplets was maintained in a humidified microscopic stage-top incubator at 37° C. and 5% $CO_2$ for the duration of the experiment. All time-lapse images were obtained by automated software control, where the Zen imaging program (Zeiss) was set to travel to specific x, y, and z positions at every 5 minutes for a total period of 6-8 hours. Image processing and analysis was done with Image) (sbinfo.nih.gov/ij/), Microsoft Office Excel 2010, and Origin Pro software. Fluorescent intensity of the cells at every time point was analyzed by selecting the region of interest (i.e., the cell body) and measuring mean intensity in ImageJ. Normalized fluorescent intensity (NFI) for each cell was calculated as a ratio of fluorescent intensity at every time point with respect to fluorescent intensity at the initial time. Contact periods were defined as cells forming visible conjugates for at least two consecutive time points. All periods of association and dissociation were counted for each cell and represented as percentage of total cells analyzed. NK-mediated cytolysis of target cells was characterized by >80% loss of calcein AM fluorescence from the target cells. Killing time for contact-dependent target death was defined as the time elapsed from the initiation of contact to loss of fluorescence (as described above). Killing time for contact-independent cell death was calculated from the start of the imaging period to the target death.

All statistical analysis was performed using Student t test, and p value <0.05 was considered statistically significant. Distribution of dynamic parameters such as contact time and killing time are represented as box-plots indicative of median, 25% and 75% quartile and outliers.

Example 2

Microfluidic Device Design and Cell Co-Encapsulation

A schematic illustration of the microfluidic nanoliter droplet array is shown in FIG. 1. The device consists of three perpendicularly oriented inlets for introducing two or three types of cells (e.g., T cells, DC, NK cells, cancer cells) and/or reagents in the aqueous phase and a channel for the oil phase (FIG. 1A). Robust monodisperse droplet generation was observed by shearing the aqueous flow by the oil phase at a flow-focusing zone (FIG. 1B). The droplet generation junction is followed by a large docking array consisting of 1000 trapping sites, where the droplets are stably arrested. Consistent droplet sizes of about 100 μm diameter (i.e., 520 pL volume) were obtained by optimization of the flow rates of the two phases (FIG. 1C). By coordinating individual inlet flow rates and optimizing initial cell density, large numbers of droplets were routinely obtained with co-encapsulation of the two or three desired types of individual cells (FIG. 1D).

Several types of cell co-encapsulation were obtained with this approach, including cell combinations for studying T-DC interaction, T-DC-cancer cell interaction, and NK-cancer cell interaction. Unstimulated T cells derived from the non-adherent fraction of peripheral blood mononuclear cells and mature DCs generated from adherent mononuclear cells cultured with cytokines were added through separate inlets to ensure that cell pairing and subsequent activation occurred only in the droplets. Likewise, NK cells and cancer cells were co-encapsulated in droplets by flowing through separate fluid inlets, allowing monitoring of early signaling events and synapse formation. For the studies with two cell types, the third inlet was used to perfuse medium. Since droplets provide a culture platform highly compatible with non-adherent cells, a number of morphological features of the encapsulated cells could be obserfed, including secretory vesicle formation (FIG. 1E), dendrite extension by DCs (FIG. 1F), and membrane blebbing prior to cell death (FIG. 1G). Results obtained by the inventors show both continuous and intermittent interactions between cell pairs, leading to quantitative analysis of dynamic parameters corresponding to these interactions (FIGS. 2A-2D). In addition, all cellular secretions remain undiluted within the droplets, leading to non-contact-mediated activation of co-encapsulated cells while minimizing stimulation of neighboring cells.

The viability of various primary cells and cell lines was tested in the droplets following individual and joint encapsulation. Lymphocytes showed more than 75% viability in the droplet array device. RPMI-8226 cells had 88% viability in the droplets after 2 hours and 72% after 7 hours.

Example 3

Co-Encapsulation of NK Cells with Myeloma Cells

Figures 3A, 3B, 3C, 3D, 3E:
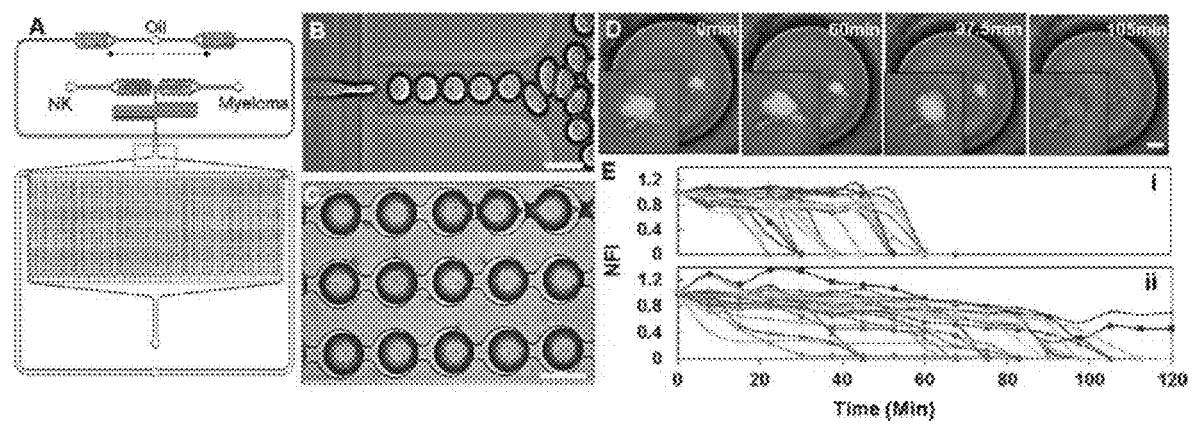
FIGS. 3A-3E show the results of an experiment co-encapsulating NK and MM cells. (3A) Schematic representation of integrated droplet generation and microarray device. (3B) Generation of picoliter droplets. (3C) Droplets loaded in microarray for stable docking. Scale bar (3B-3C): 200 mm. (3D) Time course of one NK cell-target cell pair conjugation and target death in droplet. Inset: Magnified image of NK cell (labeled with Hoechst) and target cell (labeled with calcein and Hoechst). Scale bar: 20 um. (3E) Target cell response trends: (i) Rapid cell lysis and death indicated by abrupt loss of calcein fluorescence. (ii) Gradual death indicated by slow decrease in fluorescence. NFI: normalized fluorescence intensity.

NK cells were co-encapsulated with target cells in picoliter droplets in an integrated microfluidic array to quantify cytotoxicity. The NK cells were incubated through one inlet of the device and RPMI-8226 cells, a multiple myeloma (MM) line, through the other inlet (FIG. 3A). The two cell types did not make contact in the short serpentine segment due to laminar flow of the aqueous stream. Droplets containing cells or cell pairs were generated robustly at the flow focusing zone and trapped in the docking array for live imaging and analysis (FIG. 3B). The volume of the droplets was maintained at about 520 pL. The docking array allowed trapping of 1000 droplets per experiment (FIG. 3C). Co-encapsulation of heterotypic cell pairs followed Poisson probability, resulting in droplets containing 0-2 cells of each type as well as blank droplets. For the purposes of NK-mediated cytotoxicity analysis, droplets containing a 1:1 ratio of effector (E) and target (T) cells were monitored for up to 10 hours (FIG. 3D). Viability of primary human NK cells and RPMI-8226 cells was assessed in the same experiment from droplets containing individual cells of each type. RPMI-8226 cells showed 90% viability in droplets throughout the duration of the experiment, and NK cells showed 95.38% viability in the droplets.

Example 4

NK Cell Conjugation and Target Cytolysis

NK cell mediated myeloma cell cytolysis was studied in droplets by labeling the MM target cells with calcein AM off-chip. Target cell lysis and death was defined by the fluorescence intensity of calcein, which decreases sharply due to leakage from the damaged cell membrane. Morphologically, cell membrane blebbing and rupture were observed in cells showing significant loss of calcein. Co-encapsulation of NK cells with RPMI-8226 (MM) cells resulted in >96% target cell death as determined by the loss of calcein, whereas RPMI-8226 cells alone showed 90% survival. In the droplets, NK cells initially depicted motility towards the target cell and morphological changes, including cell elongation and uropod formation (FIG. 3D). Following immune complex formation with the target, NK cells primarily remained conjugated until target cell lysis (FIG. 3D). However, 8.34% of the complexes detached and the NK cell moved away before the target cell underwent lytic death. In these instances, 42.85% of target cells ruptured within 15 min of detachment while 22.2% required >60 min. Potentially, these cells could have died because of a lytic hit delivered during conjugation followed by a delay in visible signs of death or due to NK-secreted cytotoxic molecules that affected the cells after NK detachment.

Two primary profiles of target lysis were observed: (a) target cells demonstrated minimal fluctuation in calcein intensity until the cell enlarged briefly before rupture and immediate loss of fluorescence, indicating fast death; and (b) slow death distinguished by gradual decay in calcein intensity over time. While the first group of cells showed >80% loss of calcein intensity within the first 60 minutes, the second group retained fluorescence for longer duration (FIG. 3E). In both instances, cell death was confirmed as visible cell swelling and bursting, indicating that the underlying mechanism of death was the same for both categories of cells. NK-mediated 293T death was classified as either apoptosis or necrosis based on fast or slow kill and cell blebbing. In this study, the morphological indicators of myeloma cell death in droplets were consistent with necrosis.

Figures 4A, 4B, 4C, 4D:
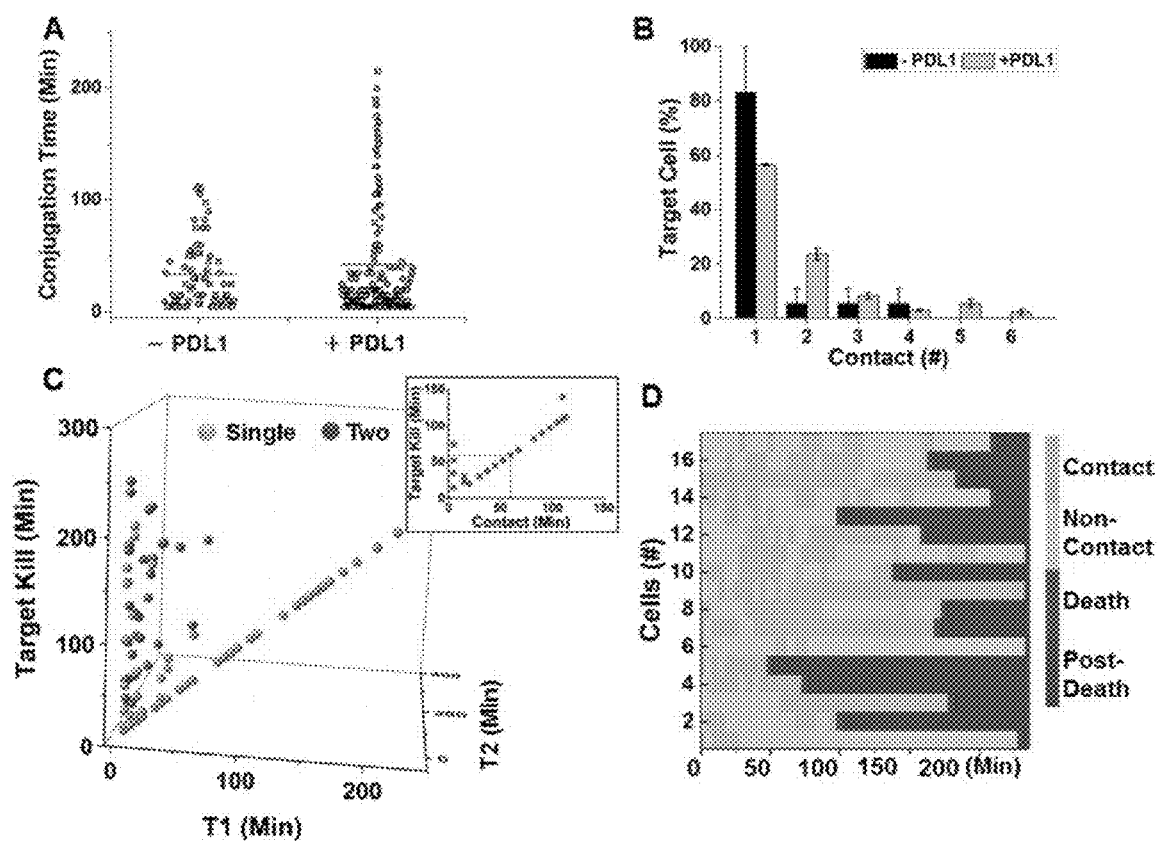
FIGS. 4A-4D show results of dynamic characterization of interactions between NK and MM cells. (4A) Duration of contact between NK cells and RPMI-8226 cells, untreated (−PD-L1) or pre-treated with 23 nM of anti-PD-L1 blocking antibody (+PD-L1) for 24 hrs prior to co-encapsulation with droplets. The mean value indicated (by −) is shown for each distribution. (4B) Number of contacts made between NK and target cell pair in a droplet (mean I SEM). (4C) Representative experiment showing killing efficiency when PD-L1-treated target cells made one (indicated by green circles) or two (red circles) consecutive contacts with NK cell, resulting in target death. The first and second contact durations are specified as T1 and T2 respectively. Inset: Killing efficiency in case of single contact-dependent target cell death in control (−PDL1) condition. The dotted line indicates 60 min, the threshold for fast target killing. (4D) Heterogeneity in target cell death following multiple short interactions in the presence of anti-PDL1 blocking antibody. Each row represents the response of one cell over the time-course.
Figures 5A, 5B, 5C, 5D:
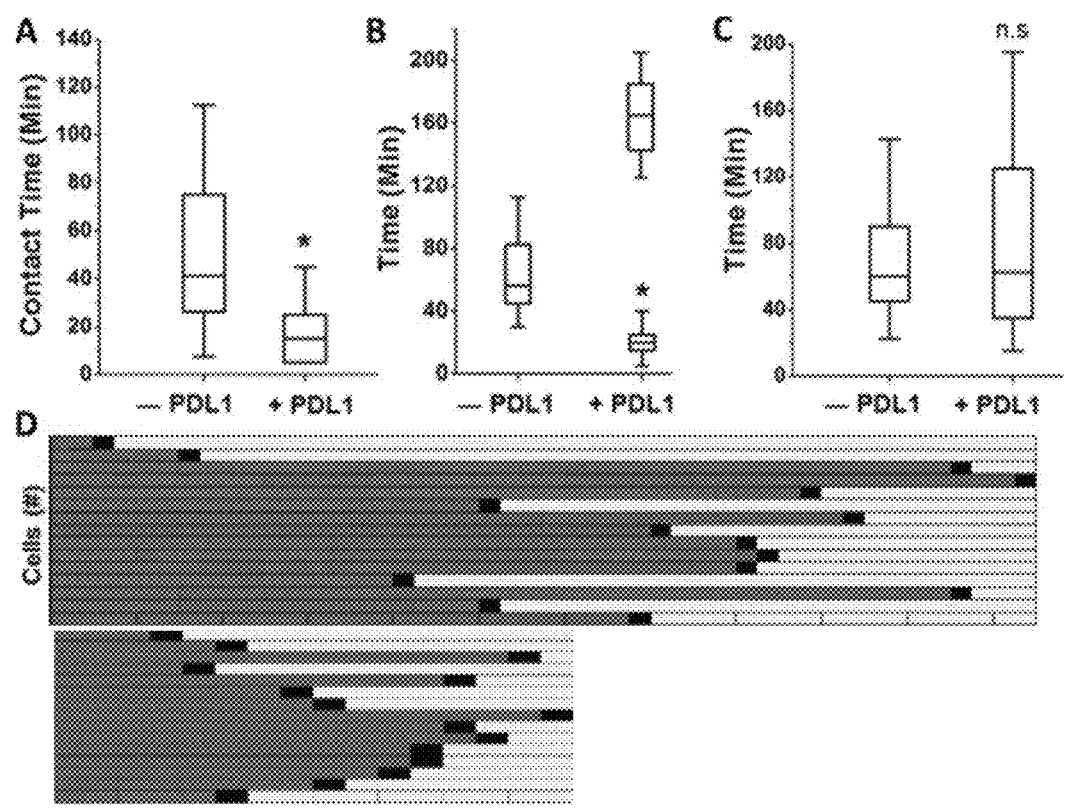
FIGS. 5A-5D show the results of dynamic characterization of interactions between NK and MM cells. (5A) Duration of contact between NK cells and RPMI-8226 cells, untreated (−PD-L1) or pre-treated with 23 nM of anti-PDLI blocking antibody (+PDLI) for 24 hours prior to co-encapsulation with droplets (*p<0.05). (5B) Killing time in case of contact-dependent target cell death in droplets (*p<0.05). In the presence of anti-PDL1 Ab (+), the target cells can be divided into two distinct sub-population, cells that died in <40 min, and cells that died in >100 min. (5C) Killing time in case of contact-independent target cell death (n.s: not significant). (5D) Top Panel: Representative heat map depicting heterogeneity in NK-target cell interaction in the presence of anti-PDLI blocking antibody. Each row represents the response of one cell over the time-course. Bottom panel: NK-target cell interaction in the absence of anti-PDL 1 blocking antibody.

The dynamic profiles of target conjugation, delivery of lytic hit and cell death in the droplets were determined. There was strong heterogeneity in the duration of conjugation between the target cells and NK cells (FIG. 4A). In the absence of anti-PDL1 antibody, more than 80% of the NK cells contacted the target cells only once (FIG. 4B). A much smaller proportion (17%) of NK cells formed 2-4 contacts with the same target cells.

Killing efficiency was assessed by determining the conjugation time needed for the NK cells to deliver a cytotoxic hit (FIG. 4C, Inset). Cells that mediated fast kill in <60 min of contact were considered efficient killers (60%). Overall, the time required for target cell death following contact varied from 15-140 minutes. Contact-mediated interactions resulted in 98±2.8% target death in droplets, suggesting highly functional anti-tumor activity by these cells.

Cytolytic lymphocytes can kill multiple target cells sequentially. Small populations of NK cells have been deemed "serial killers" due to their ability to kill 4 or more targets within 16 hrs. In this study, such events were observed at a frequency of 8.3% in shorter periods (90 min). An NK cell sequentially lysed two target cells following 30 and 60 min of contact. Another NK cell contacted four RPMI-8226 cells simultaneously and mediated target cell death at 30, 30, 37.5 and 75 min respectively.

The death of target cells without direct contact with NK cells was also observed. In this study, 46.0±0.91% of the events monitored resulted in RPMI-8226 cells developing massive membrane damage and death without NK cell conjugation, although the time required for cell lysis showed a similar spread with respect to contact-mediated death. Stress-related RPMI-8226 cell death in droplets was ruled out by analyzing cell viability over a period of 6 hours. Thus, the contact-independent target cell deaths are believed due to constitutive secretion of granzymes by NK cells, Fas ligand, perforin-containing exosomes, or a combination thereof. It is feasible that once the secreted perforins are internalized by RPMI-8226, GrzB further facilitated cell death without direct contact. Since cell secretions were compartmentalized in picoliter droplets, they accumulate over time and enable faster reaction at lower effector-to-target ratio compared to standard culture conditions where secreted products are diluted in large volumes of medium.

Example 5

Immunotherapeutic Regulation of Myeloma Cell Lysis by NK Cells

The impact of the PD-UPD-LI axis in regulating dynamic cell interaction and target cell death by NK cells was investigated. When RPMI-8226 cells were pre-treated with an anti-PD-L1 blocking antibody, a change in the duration of contact between NK and target cells was observed (FIG. 4A). Although the mean conjugation periods did not differ significantly between untreated and anti-PDLI antibody treated cells, 32.56% of treated cells were observed to have more than 150 min of contact, which was not observed in untreated cells. 47.6±3.38% of target cells detached from the NK cells before death (compared to 8.34% of control cells). The NK and myeloma cells formed serial contacts in the presence of anti-PDLI antibody instead of single long-lasting contacts, resulting in 2.6 times greater number of multiple (2-6) contacts between each cell pair (FIG. 4B).

Killing efficiency of NK cells was more varied in the presence of anti-PDLI antibody. 49.12% of target cells that made single contacts with NK cells underwent fast death resulting from <60 min of contact (FIG. 4C). Two clusters of cells were detected: one exhibited stable, long-lasting conjugates until target death, and the other exhibited shorter contact periods followed by target death at later time points. Cells that underwent two contacts depicted short periods of first contact (T1) ranging from 10-60 min. The second contact (T2) was of similar duration, except in 15% of cells where the contact ranged from 60-190 min. Similar heterogeneities were observed in the small number of cells that made >2 contacts (FIG. 4D). The delay in death times of individual cells following contact could result from either an inefficient killing mechanism of NK cells or impaired formation of immune synapses.

The RPMI-8226 cells undergoing contact-independent lysis did not show a significant difference in killing duration in the absence or presence of PD-L1 blockade (66.5 vs. 79.6 minutes respectivel). Potentially, secretion of cytolytic molecules such as perforin and granzyme by NK cells were unaffected by the PD-LI blockade, at least in the short term, and therefore continued to mediate target cell lysis in droplets.

At a 1:1 ratio of the two cell types, there was no statistical difference in the immune complex formation in the presence or absence of anti-PD-L1 treatment, implying that the effect of PD-L1 blockade does not rely merely on receptor-ligand interaction.

Example 6

A Model of NK Cell Function with Modulation of the PD-1/PD-L1 Pathway

Figures 6A, 6B, 6C:
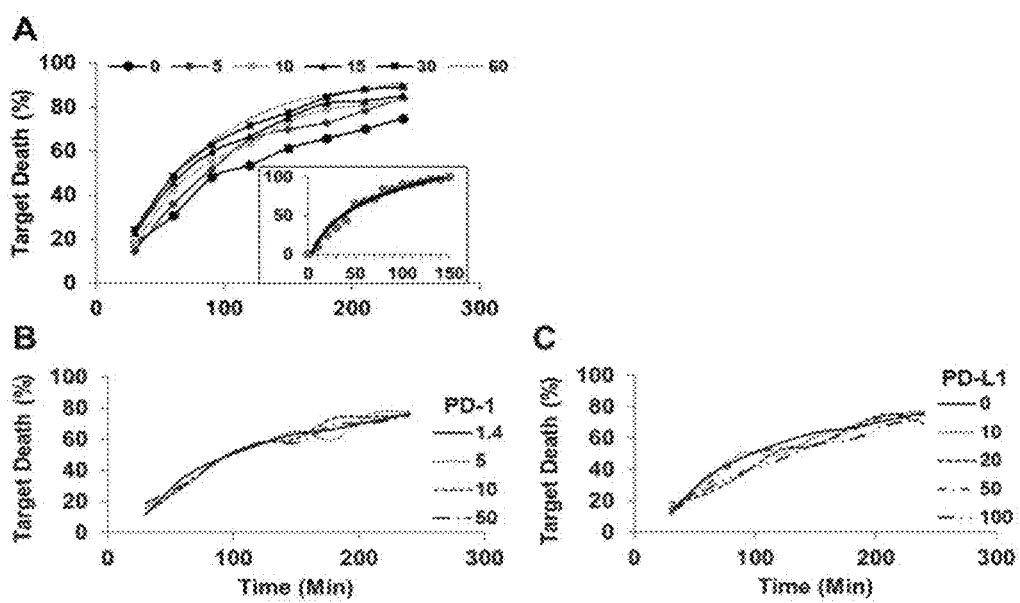
FIGS. 6A-6C show the results of computational analysis of NK cell-target cell contacts. (6A) NK cell-mediated target cell death (%) increases in droplets with increase in contact distance (re). re=0 indicates direct contact between the cells; re=5−60 indicates a distance of 5-60 lam between the cells. Increasing re accounts for target cell death due secretion of lytic molecules in proximal cells. Inset: Experimental data showing cumulative target cell death (%) along Y-axis over Time (min, X-axis). The trendline indicates logarithmic increase in cell death. (6B-6C) Prediction of target cell death at re: 0 based on expression PD-1/PDL1 pathway. (6B) Increase in PD-1 only, setting PD-L1: 0. (6C) Increase in PD-L1 only, setting PD-1:1.4.

To determine the impact of PD-1/PDL1 pathway on NK functionality, a combination of experimental and mathematical techniques was employed. Based on the variability in lytic interaction between NK and target cells in droplets, an agent based model (ABM) was developed to simulate the dynamics of contact-mediated cytolysis. This approach allowed for more detailed analysis of the status of the individual cells and cell interactions rather than population-based models. A Monte Carlo-type simulation was incorporated to average over all the results. The first model accounts for the various phases of cellular interaction: motility of NK cells towards target cells, conjugation, delivery of lytic hit, and target death. Contact-mediated target death increased over time in a logarithmic manner (FIG. 6A). Increasing the gap, or contact distance ($r_c$), from 0 to 60 µm allowed consideration of cells that made contact but detached before target death, as observed experimentally. The model simulations showed that the dynamic trends of target death are consistent with experimental findings (FIG. 6A). It has been argued that there is an inherent delay in NK-mediated target death (5 hrs), which could be due to the lag time between lytic hit and actual cell death, or due to the necessity of priming NK cells. At the single cell level, significant death was observed within 60 min in droplets (FIG. 6A, inset); therefore, no delay time or priming factors were included in the model.

The impact of variable expression of the PD-1/PD-L1 pathway on NK functionality was assessed. Although primary human CD56$^+$ CD3$^-$ NK cells isolated from healthy donors express PD-1 minimally, it is inducible after IL-2 treatment. The IL-2 pathway has previously been implicated in myeloma. Therefore, the effect of increasing PD-1 expression on NK cell cytolytic capacity was included in the model (FIG. 6B). Increasing PD-1 expression from 1.4% (mimicking healthy NK cells) to 50% (mimicking advanced MM) showed no change in target death if there was no corresponding expression of PD-L1. Likewise, expression of PD-L1 alone did not change myeloma death in the model (FIG. 6C). PD-1 levels were kept constant at 1.4%. However, increasing both PD-1 and PD-L1 simultaneously inhibited target death.

Figures 7A, 7B, 7C:
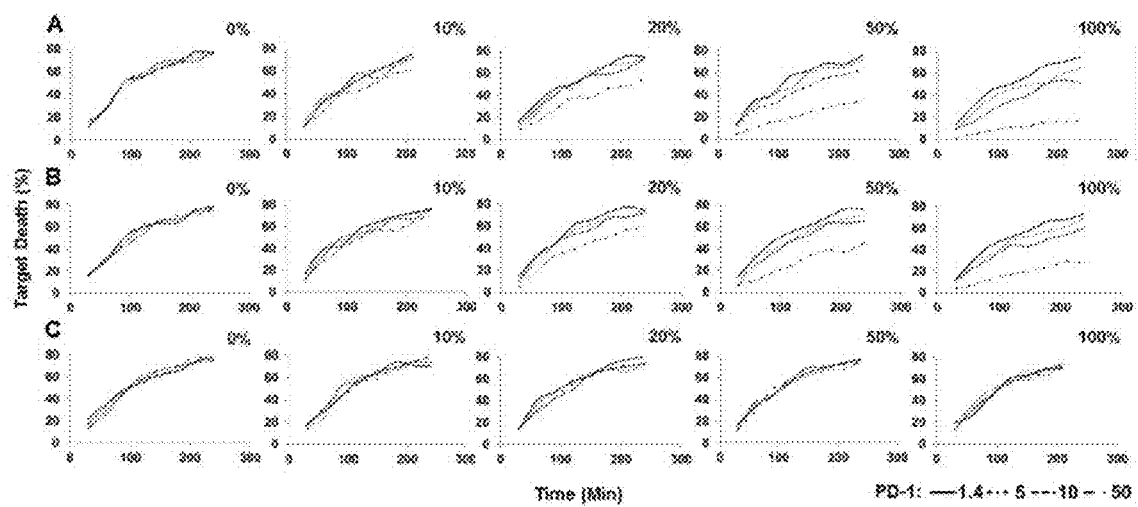
FIGS. 7A-7C show the effects of inhibition of the PD-1/PD-L1 pathway at varying efficiencies. (7A) 25% efficiency, (7B) 50% efficiency, and (7C) 100% efficiency. Each graph shows % of NK cells expressing PD-1 at increasing levels (1.4-50). Drug efficiency was further modeled at increased levels of PD-L1 expression on tumor cells: 0%, 15%, 20%, 50% and 100%. Target death % decreases with concomitant increase in PD-1 and PD-L1. However, at 100% drug efficiency the effect of PD-1 or PD-L1 is negligible.

The effect of inhibiting the PD-1/PD-L1 pathway via an immunomodulatory agent was then modeled. Treatment with lenalidomide is known to decrease PD-L1 expression, and a monoclonal antibody against PD-1 is known to increase efficacy of NK effector functions. Assuming that the drug operates at maximum efficacy ($E_{max}$), addition of a drug was observed to restore maximum efficacy of NK-mediated cytolysis of target cells despite 100% expression of PD-L1 and 50% expression of PD-1 (FIG. 7C). At decreasing values of $E_{max}$ (25-50%), NK cell function was governed by both PD-1 and PD-L1 expression on NK and myeloma cell respectively (FIGS. 7A and 7B).

The efficacy of a drug that affects receptors, as is the case with PD-1/PD-L1 interference, is dependent on a number of factors, but most importantly affinity and intrinsic activity. Drugs with lower affinity or sub-optimal activity in bound form would not be effective in inhibiting cell responsiveness. Since the two ligands of PD-1, PD-L1 and PD-L2, bind with distinct affinities, the efficacy of a drug that affects this pathway must be carefully characterized in specific cell types. Although the model did not distinguish affinity from activity, it serves as a preliminary method of assessing the effect of PD-UPD-L1 blockade on cells at varying stages of expression in myeloma cells.

Example 7

Dynamic Profiling of Immunological Synapse and DC-T-Cell Tracking

Figures 2A, 2B, 2C, 2D:
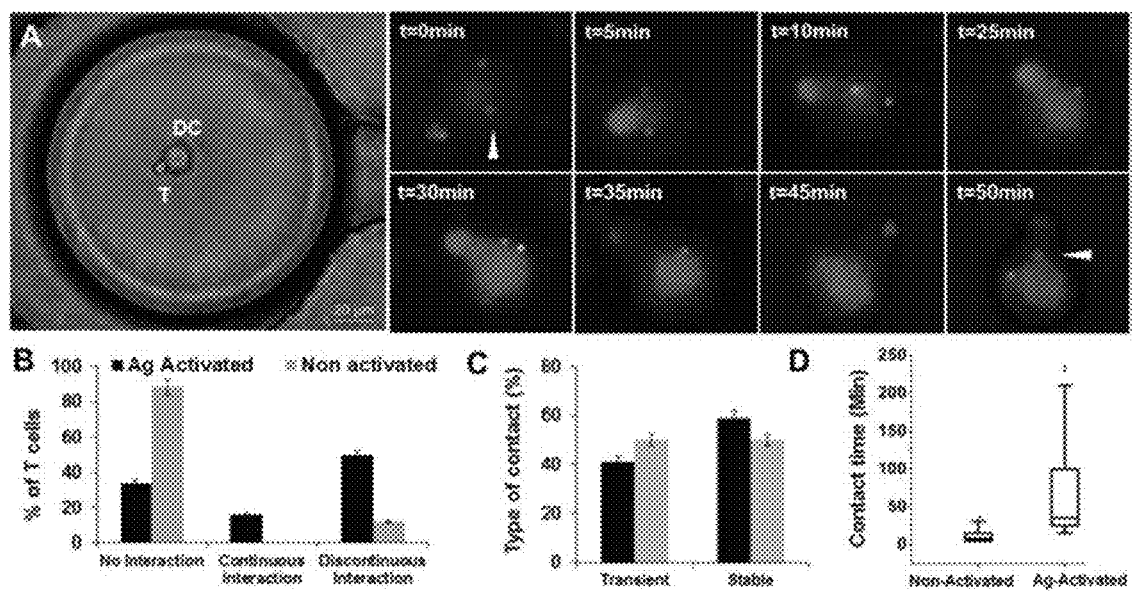
FIGS. 2A-2D show the results of dynamic monitoring of interactions between DC and T cells. (2A) DCs were pulsed with OVA-FITC (100 ug mL$^{-1}$, 16 hours) and CCL21 (25 ng 2 hours) and co-encapsulated with untreated T cells in droplets. OVA-FITC expression on DC surface is indicated by arrowheads. T cells are labeled with CMTPX tracker (red), which is transferred to the DCs over time. Images were obtained every 5 minutes. Scale bar: 20 um, (2B) Analysis of the types of interaction between DC and T cells: no interaction over a period of 5 hours, continuous interaction due to conjugate formation and discontinuous interaction defined by short periods of attachment and detachment. DCs were either activated by pre-treatment with OVA-FITC and CCL2 I (Ag activated) or untreated (non-activated). (2C) Cells undergoing discontinuous interaction were further categorized into transient (<10 minutes of contact) and stable (>10 minutes) interaction. (2D) Distribution of contact times between DC and T cells (outliers are indicated).

It was previously shown that co-encapsulation of DCs with T cells in droplets results in establishment of physical contact between the cells and reorganization of tubulin networks. The polarization of cytoskeletal components, including F-actin and tubulin, promotes active transport of signaling molecules, endocytosis and receptor-mediated cellular communication at the intercellular synapse (IS). In this study, the dynamics of IS formation between DC and T cells was probed. Mature DCs that had not specifically been loaded with Ag demonstrated relatively low interaction with non-stimulated T cells. Among the DC-T cell pairs co-encapsulated, 11% cells showed short periods of interaction while most did not interact at all (FIG. 2B). The duration of these interactions was either less than 10 minutes (50%), or 10-20 minutes (33%) (FIG. 2B). No interaction lasted longer than 35 minutes.

Dynamic interactions of chemokine (CCL21) treated, Ag-loaded DCs and naïve T cells was studied. DCs were exposed to FITC-conjugated OVA (323¬329) peptides overnight, followed by treatment with CCL21 before co-encapsulation in droplets with naïve T cells (FIG. 2A). The presence of lymphoid chemokines such as CCR7 ligands CCL19 and CCL21 in the lymph node is known to regulate immune cell migration, maturation and effector functions. In this study, a marked increase was observed in the extent of DC-T cell interaction upon activation compared to control conditions (FIG. 2B). The dynamic single cell analysis also revealed strong heterogeneity in cellular interactions with respect to DC-T cell conjugate formation. While 34% of the T cells monitored showed no interaction with DCs, 16% remained conjugated throughout the duration of the experiment (5 hours). The conjugated cells showed lateral movement, in that the respective positions of the T cells on the surface of the DCs changed with time (FIG. 2A, right panel). OVA-FITC peptide expressed on the surface of DCs was observed. Initially the T cell and the DC formed a synapse away from the site bearing the OVA-FITC peptide, but the contact site altered over time and eventually settled at the site of the Ag at 50 minutes. This motility of T cells observed in almost all T-DC conjugates; however, the time required to reach the Ag-bearing site varied widely from cell to cell.

A large proportion of the T cells observed (50%) interacted discontinuously and asynchronously with the co-encapsulated DCs, forming short term contacts and disassociating repeatedly (FIG. 2B). Here, transient interaction was defined by <10 minutes of cell complex retention. Longer interactions were considered stable. As indicated in FIG. 2C, 58% of the T cells undergoing discontinuous interaction depicted periods of stable contacts. While the duration of the contacts varied cell to cell, majority of the contacts lasted <40 minutes (FIG. 2D).

Figure 8:
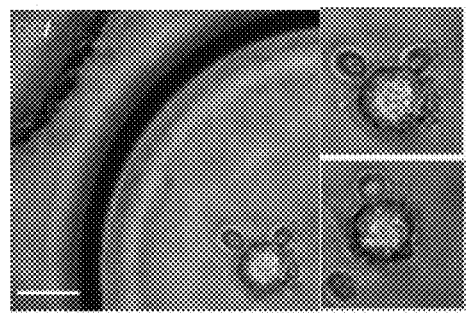
FIG. 8 shows interactions among multiple cells in microdroplets. DCs (green) were activated with OVA-FITC and CCL2 I. The T cells were untreated and labeled with CMTPX (red) tracker. The panels (phase, fluorescent and overlay) depict DC and T cells at various time points 25 min (left), 15 min (top right), and 35 min (bottom right). Scale bar: 20 µm.

The initial cell density of the two populations was increased, and interactions between multiple cells were observed (FIG. 8). In the lymph nodes, DCs scan T cells at a rapid pace in a largely random manner. This process was modeled in droplets by co-encapsulating two or more T cells with DCs. A single DC could interact with more than one T cell simultaneously but not vice versa. In all instances of multiple cell encapsulation, some DCs were found to be more reactive than others, as the T cells essentially interacted with one DC during the observation period. As shown in FIG. 3, two of the T cells remained conjugated with the DC, while the third cell dissociated but did not interact with the other DCs present in the droplet. This demonstrates heterogeneity in the dynamic events occurring in immunological synapse formation and establishes the suitability of the droplet microfluidic platform in assessing spatiotemporal dynamic events during an immune response.

Example 8

Activation of T Cell Effector Functions In Vitro by DC-Based Vaccines

Figures 9A, 9B, 9C, 9D, 9E, 9F:
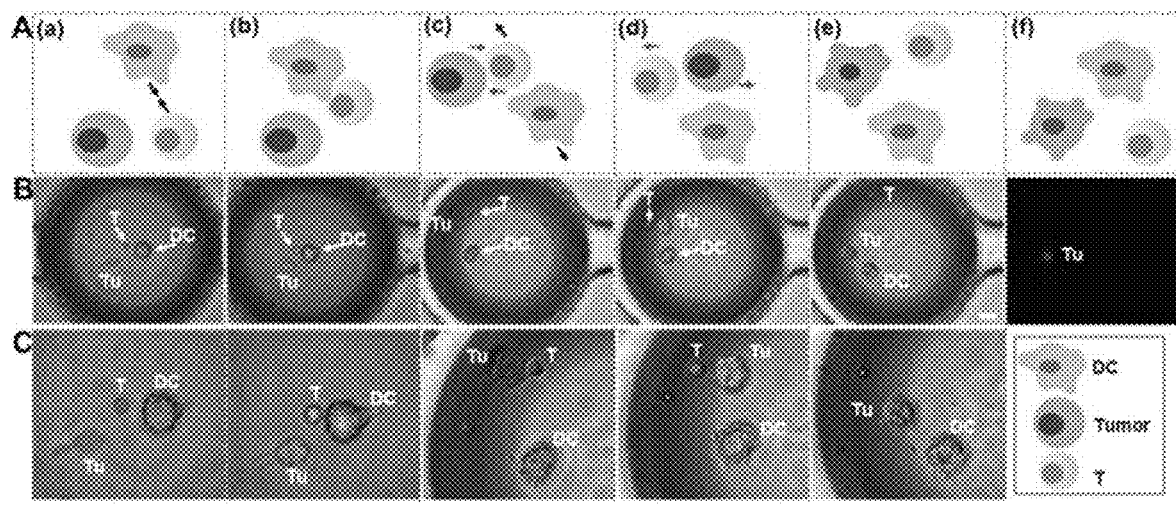
FIGS. 9A-9C show results of a co-encapsulation of tumor lysate-pulsed DC, T cells, and tumor cells (RPMI 8226). (9A) The top panel illustrates the various stages of interaction between the immune and tumor cells. Movement of DC and T cells are indicated by black arrow while movement of T and tumor cells are indicated by red arrow. (panel a) Freely motile DC and T cells move towards each other within droplets. (panel b) DC-T conjugates are formed. (panel c) DC-T conjugates dissociate and cells become motile again. T cells and tumor cells move towards each other and establish contact. (panel d) T cells dissociate from tumor. (panel e) Tumor cells depict morphological changes, blebbing and membrane rupture. (panel f) Tumor cell death indicated by uptake of ethidium homodimer. (9B) Microscopic images of specific stages of interaction described in (9A) observed in droplets. (9C) Magnified images of the corresponding panels in (9B). Scale bar: 20 µm.

The efficacy of DCs expressing tumor antigen in priming of T cell effector responses against a MM cell line was investigated in droplets. DC vaccine cells were activated with tumor lysate and DC/MM fusion cells. DCs matured by exposure to RPMI-8226 cell lysates, were co-encapsulated with unprimed T cells and RPMI-8226 cells in droplets. All three cells were initially separate and freely mobile, as illustrated schematically in FIG. 9A and demonstrated in droplets in FIGS. 9B and 9C. Sequential interaction of these cell types occurred in the droplets, with DCs interacting with T cells first (FIG. 9B), followed by T-cancer cell interaction (FIG. 9C), thereby recapitulating the succession of events observed physiologically. Three distinct time phases were observed in the droplets. First, the DCs loaded with tumor antigens demonstrated transient physical contact with T cells on the order of 10-20 minutes or less. Then the DC and T cells separated and a variable period of segregation was observed, during which all three cell types remained unattached. In the third phase, T cells formed conjugates with the RPMI-8226 cells for a period of about 20-30 minutes, which ended with cancer cell death. These interactions took place over a total time period of 2 hours, although the duration of DC-T interaction and T-cancer interaction was heterogeneous between droplets. Furthermore, cancer cell death occurred in two ways, either in conjugation with the T cell or following separation of the cancer-T cell complex. Cancer cell death was most commonly observed by cell blebbing and membrane rupture, as well as uptake of ethidium homodimer. These results demonstrate that presentation of whole tumor derived antigen as lysate or DC/tumor hybridoma results in the productive interaction between DC and T cells resulting in T cell activation. While T cell activation appeared to be dependent on the presence of antigen, killing in this model was directed against allogeneic myeloma cell lines.

A similar effect was observed in RPMI-8226 cells when co-encapsulated with DC/MM fusion cells. DCs were fused with RPMI-8226 cells by incubating the cells in the presence of PEG. The fusion cells interacted with T cells, as indicated by the conjugation of the two cell types, followed by T cell-cancer cell interaction and cancer cell death, preceded by membrane blebbing and large-scale cellular vesiculation.

The present application file contains drawings executed in color. Copies of the patent or patent application publication with color drawings will be provided by the United States Patent and Trademark Office upon request and payment of the necessary fee.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present technology has been described in conjunction with certain preferred embodiments, one of ordinary skill, after reading the foregoing specification, will be able to effect various changes, substitutions of equivalents, and other alterations to the compositions and methods set forth herein.

REFERENCES

1. Elowitz, M. B., Levine, A. J., Siggia, E. D. & Swain, P. S. Stochastic gene expression in a single cell. *Science*. 297, 1183-1186 (2002).
2. Raj, A., Peskin, C. S, Tranchina, D, Vargas, D. Y. & Tyagi, S. Stochastic mRNA synthesis in mammalian cells. *PloS Biol*. 4(10), e309 (2006).
3. Cheng, Y. & Newell, E. W. Deep Profiling Human T Cell Heterogeneity by Mass Cytometry. *Adv Immunol*. 131, 101-134 (2016).

4. Chattopadhyay, P. K, Roederer, M. Good cell, bad cell: flow cytometry reveals T-cell subsets important in HIV disease. *Cytometry A.* 77, 614 (2010).
5. Nawaz, A. A, Chen. Y., Nama, N., Nissly, R. H., Ren, L., Ozcelik, A., Wang, L., McCoy, J. P., Levine, S. J, & Huang, T. J. Acoustofluidic Fluorescence Activated Cell Sorter. *Anal Chem.,* 87, 12051-12058 (2015).
6. Marr, C., Zhou, J. X & Huang, S. Single-cell gene expression profiling and cell state dynamics: collecting data, correlating data points and connecting the dots. *Curr Opin Biotechnol.* 39, 207-214 (2016).
7. Konry, T., Sarkar, S., Sabhachandani, P. & Cohen, N. Innovative Tools and Technology for Analysis of Single Cells and Cell-Cell Interaction. *Annu Rev Biomed Eng.* 259, 259-284 (2016).
8. Guo, F., French, J. B., Li, P., Zhao, H., Chan, C. Y. Fick, J. R., Benkovic, S. J & Huang T. J. Probing cell-cell communication with microfluidic devices. *Lab Chip.* 13, 3152-3162 (2013).
9. Omelchenko, T., Fetisova, E., Ivanova, O., Bonder, E. M., Feder, H., Vasiliev, J. M. & Gelfand, I. M. Contact interactions between epitheliocytes and fibroblasts: formation of heterotypic cadherin-containing adhesion sites is accompanied by local cytoskeletal reorganization. *Proc Natl Acad Sci U S A.* 98, 8632-8637 (2001).
10. Chao, D. L., Ma, L., & Shen, K., Transient cell-cell interactions in neural circuit formation. *Nat Rev Neurosci.* 10, 262-271 (2009).
11. Orange, J. S. Formation and function of the lytic NK-cell immunological synapse. *Nat Rev Immunol.* 8, 713-725 (2009).
12. Fauriat, C., Long, E. O., Ljunggren, H. G. & Bryceson Y. T. Regulation of human NK-cell cytokine and chemokine production by target cell recognition. *Blood.* 115, 2167-2176 (2010).
13. Eissmann, P. & Davis, D. M. Inhibitory and regulatory immune synapses. *Curr Top Microbiol Immunol.* 118, 63-79 (2010).
14. Barreira da Silva, R., Graf, C & Munz, C. Cytoskeletal stabilization of inhibitory interactions in immunologic synapses of mature human dendritic cells with natural killer cells. *Blood.* 118, 6487-6498 (2011).
15. Deguine, J., Breart, B., Lemaitre, F., Di Santo, J. P., & Bousso, P. Intravital imaging reveals distinct dynamics for natural killer and CD8(+) T cells during tumor regression. *Immunity.* 33, 632-644 (2010).
16. Lopez, J. A., Susanto, O., Jenkins, M. R., Lukoyanova, N., Sutton, V. R., Law, R. H., Johnston, A., Bird, C. H., Bird, P. I., Whisstock, J. C., Trapani, J. A, Saibil, H. R & Voskoboinik, I. Perforin forms transient pores on the target cell plasma membrane to facilitate rapid access of granzymes during killer cell attack. *Blood.* 121, 2659-2668 (2013).
17. Davis, D. M. Mechanisms and functions for the duration of intercellular contacts made by lymphocytes. *Nat Rev Immunol.* 9, 543-555 (2009).
18. Yamanaka, Y. J., Berger, C. T. Sips, M. Cheney, P. C., Alter, G. & Love, J. C. Single-cell analysis of the dynamics and functional outcomes of interactions between human natural killer cells and target cells. *Integr Biol (Camb).* 4, 1175-1184 (2012).
19. Vanherberghen, B., Olofsson, P. E., Forslund, E., Sternberg-Simon, M., Khorshidi, M. A, Pacouret, S., Guldevall., Enqvist, M., Malmberg, K. J., Mehr, R. & Önfelt, B. Classification of human natural killer cells based on migration behavior and cytotoxic response. *Blood.* 121, 1326-34 (2013).
20. Olofsson, P. E., Forslund, E., Vanherberghen, B., Chechet, K., Mickelin, O., Ahlin, A. R., Everhorn, T & Onfelt, B., Distinct Migration and Contact Dynamics of Resting and IL-2-Activated Human Natural Killer Cells. *Front Immunol.* 5, 80 (2014).
21. Iwai, Y., Ishida, M., Tanaka, Y., Okazaki, T., Honjo, T., Minato, N. Involvement of PD-L1 on tumor cells in the escape from host immune system and tumor immunotherapy by PD-L1 blockade. *Proc Natl Acad Sci U S A.* 99, 12293-12297 (2002).
22. Zitvogel, L & Kroemer, G. Targeting PD-1/PD-L1 interactions for cancer immunotherapy. *Oncoimmunology.* 1, 1223-1225 (2012).
23. Madore, J., Vilain, R. E., Menzies, A. M., Kakavand, H., Wilmott, J. S., Hyman, J.,Yearley J. H., Kefford, R. F., Thompson, J. F., Long, G. V., Hersey, P & Scolyer, R. A., PD-L1 expression in melanoma shows marked heterogeneity within and between patients: implications for anti-PD-1/PD-L1 clinical trials. *Pigment Cell Melanoma Res.* 28, 245-253 (2015).
24. Guldevall, K., Brandt, L., Forslund E., Olofsson, K., Frisk, T. W., Olofsson, P. E., Gustafsson, K., Manneberg, O., Vanherberghen, B., Brismar, H., Kärre, K., Uhlin, M & Onfelt, B. Microchip Screening Platform for Single Cell Assessment of NK Cell Cytotoxicity. *Front Immunol.* 7, 119 (2016).
25. Chen, F., Zhan, Y., Geng, T., Lian, H., Xu, P. & Lu, C. Chemical transfection of cells in picoliter aqueous droplets in fluorocarbon oil. www.ncbi.nlm.nih.gov/pubmed/21967571, *Anal Chem.* 83, 8816-8820 (2011).
26. Dura, B., Dougan, S. K., Barisa, M., Hoehl, M. M., Lo, C. T., Ploegh, H. L & Voldman, J. Profiling lymphocyte interactions at the single-cell level by microfluidic cell pairing. *Nat Commun.* 6. 5940 (2015).
27. Chung, K., Rivet, C. A., Kemp, M. L & Lu, H. Imaging single-cell signaling dynamics with a deterministic high-density single-cell trap array. *Anal Chem.* 83, 7044-7052 (2011).
28. Kim, T. J., Kim, M., Kim, H. M., Lim, S. A., Kim, E. O., Kim, K., Song, K. H., Kim, J., Kumar, V., Yee, C., Doh, J. & Lee, K. M. Homotypic NK cell-to-cell communication controls cytokine responsiveness of innate immune NK cells. *Sci Rep.* 4, 7157 (2014).
29. Berger R., Rotem-Yehudar, R., Slama, G., Landes, S, Kneller, A., Leiba, M., Koren-Michowitz, M., Shimoni A & Nagler, A. Phase I safety and pharmacokinetic study of CT-011, a humanized antibody interacting with PD-1, in patients with advanced hematologic malignancies. *Clin Cancer Res.* 14, 3044-3051 (2008).
30. Herbst, R. S., Soria, J. C., Kowanetz, M., Fine, G. D., Hamid, O., Gordon, M. S., Sosman, J. A., McDermott, D. F., Powderly, J. D., Gettinger, S. N., Kohrt, H. E. K., Horn, L., Lawrence, D. P., Rost, S., Leabman, Maya., Xiao, Y., Mokatrin, A., Koeppen, H., Hegde, P. S., Mellman, I., Chen, D. S. & Hodi F. S. Predictive correlates of response to the anti-PD-L1 antibody MPDL3280A in cancer patients. *Nature.* 515, 563-567 (2014).
31. Lagus, T. P., Edd, J. F., High-throughput co-encapsulation of self-ordered cell trains: cell pair interactions in microdroplets. *RSC Adv.* 3, 20512-20522 (2013).
32. Golberg, A., Linshiz, G., Kravets, I., Stawski, N., Hillson, N. J., Yarmush, M. L., Marks, R. S & Konry, T. Cloud-Enabled Microscopy and Droplet Microfluidic Platform for Specific Detection of Escherichia coli in Water. *PLoS One.* 9, e86341. (2014).

33. Sarkar, S., Cohen, N., Sabhachandani, P & Konry, T. Phenotypic drug profiling in droplet microfluidics for better targeting of drug-resistant tumors. *Lab Chip.* 15. 4441-4450 (2015).
34. Godfrey, J & Benson Jr, D. M. The role of natural killer cells in immunity against multiple myeloma. *Leuk Lymphoma.* 53, 1666-1676 (2012)
35. Heidenreich, S., Zu Eulenburg, C., Hildebrandt, Y., Stübig, T., Sierich, H., Badbaran, A., Eiermann, T. H., Binder, T. M & Kröger, N. Impact of the NK cell receptor LIR-1 (ILT-2/CD85j/LILRB1) on cytotoxicity against multiple myeloma. *Clin Dev Immunol.* 2012, 652130 (2012).
36. Isaaz, S., Baetz, K., Olsen, K., Podack, E. & Griffiths, G. M. Serial killing by cytotoxic T lymphocytes: T cell receptor triggers degranulation, re-filling of the lytic granules and secretion of lytic proteins via a non-granule pathway. *Eur J Immunol.* 25, 1071-1079 (1995).
37. Bhat, R. & Watzl C, C. Serial killing of tumor cells by human natural killer cells—enhancement by therapeutic antibodies. *PLoS One.* 2, e326 (2007).
38. Lopez, J. A., Brennan, A. J., Whisstock, J. C., Voskoboinik, I & Trapani, J. A. Protecting a serial killer: pathways for perforin trafficking and self-defence ensure sequential target cell death. *Trends Immunol.* 33, 406-412 (2012).
39. Lugini, L., Cecchetti, S., Huber, V., Luciani, F., Macchia, G., Spadaro, F., Paris, L., Abalsamo, L., Colone, M., Molinari, A., Podo, F., Rivoltini, L., Ramoni, C., Fais, S. Immune Surveillance Properties of Human NK Cell-derived Exosomes. *J Immunol.* 89, 2833-2842 (2012).
40. Prakash, M. D., Bird, C. H & Bird, P. I. Active and zymogen forms of granzyme B are constitutively released from cytotoxic lymphocytes in the absence of target cell engagement. *Immunol Cell Biol.* 87, 249-254 (2009).
41. Ruggeri, L., Mancusi, A., Capanni, M., Urbani, E., Carotti, A., Aloisi, T., Stern, M., Pende, D., Perruccio, K., Burchielli, E., Topini, F., Bianchi, E., Aversa, F., Martelli, M. F & Velardi, A. Donor natural killer cell allorecognition of missing self in haploidentical hematopoietic transplantation for acute myeloid leukemia: challenging its predictive value. *Blood.* 110, 433440 (2007).
42. Shi, J., Tricot, G., Szmania, S., Rosen, N., Garg, T. K., Malaviarachchi, P. A., Moreno, A., Dupont, B., Hsu, K. C., Baxter-Lowe, L. A., Cottler-Fox, M., Shaughnessy Jr, J. D., Barlogie, B & van Rhee, F. Infusion of haploidentical killer immunoglobulin-like receptor ligand mismatched NK cells for relapsed myeloma in the setting of autologous stem cell transplantation. *Br J Haematol.* 143, 641-654 (2008).
43. Benson Jr., D. M., Bakan, C. E., Mishra, A., Hofmeister, C. C., Efebera, Y., Becknell, B., Baiocchi, R. A., Zhang, J., Yu, J., Smith, M. K., Greenfield, C. N., Porcu, P., Devine, S. M., Rotem-Yehudar, R., Lozanski, G., Byrd, J. C. & Caligiuri, M. A. The PD-1/PD-L1 axis modulates the natural killer cell versus multiple myeloma effect: a therapeutic target for CT-011, a novel monoclonal anti-PD-1 antibody. *Blood.* 116, 2286-2294 (2010).
44. Liu, J., Hamrouni, A., Wolowiec, D., Coiteux, V., Kuliczkowski, K., Hetuin, D., Saudemont, A & Quesnel, B. Plasma cells from multiple myeloma patients express B7-H1 (PD-L1) and increase expression after stimulation with IFN-{gamma} and TLR ligands via a MyD88-, TRAF6-, and MEK-dependent pathway. *Blood.* 110, 296-304 (2007).
45. Fife, B. T., Pauken, K. E., Eagar, T. N., Obu, T., Wu, J., Tang, Q., Azuma, M., Krummel, M. F & Bluestone, J. A. Interactions between PD-1 and PD-L1 promote tolerance by blocking the TCR-induced stop signal. *Nat Immunol.* 10, 1185-1192 (2009).
46. Almeida, C. R., Ashkenazi, A., Shahaf, G., Kaplan, D., Davis, D. M. & Mehr, R. Human NK cells differ more in their KIR2DL1-dependent thresholds for HLA-Cw6-mediated inhibition than in their maximal killing capacity. *PLoS One.* 6, e24927 (2011).
47. Vacca, A., Di Stefano, R., Frassanito, A., Iodice, G & Dammacco, F. A disturbance of the IL-2/IL-2 receptor system parallels the activity of multiple myeloma. *Clin Exp Immunol.* 84, 429-434 (1991).
48. Cheng, X., Veverka, V. Radhakrishnan, A., Waters, L. C., Muskett, F. W., Morgan, S. H., Huo, J., Yu, C., Evans, E. J., Leslie, A. J., Griffiths, M., Stubberfield, C., Griffin, R., Henry, A. J., Jansson, A., Ladbury, J. E., Ikemizu, S., Carr, M. D & Davis, S. J. Structure and interactions of the human programmed cell death 1 receptor. *J Biol Chem.* 288, 11771-11785 (2013).
49. Kuepfer, L., Peter, M., Sauer, U., Stelling. J., Ensemble modeling for analysis of cell signaling dynamics. *Nat. Biotechnol.* 25, 1001-1006 (2007).
50. Watzl, C., Sternberg-Simon, M., Urlaub, D., Mehr. R. Understanding natural killer cell regulation by mathematical approaches. *Front Immunol.* 3, 359 (2012).
51. Duffy, K. & Hodgkin, P. D. Intracellular competition for fates in the immune system. *Trends Cell Biol.*, 22, 457-464 (2012).
52. Chavali, A., Gianchandano E., Tung, K., Lawrence, M., Peirce, S & Papin. J. Characterizing emergent properties of immunological systems with multi-cellular rule-based computational modeling. *Trends Immunol.* 29, 589-599 (2008).
53. Shahaf, G., Barak, M., Zuckerman, N., Swerdlin, N., Gorfine, M & Mehr, R. Antigen-driven selection in germinal centers as reflected by the shape characteristics of immunoglobulin gene lineage trees: a large-scale simulation study. *J. Theor. Biol.* 255, 210-222 (2008).
54. Kaplan, A., Kotzer, S., Almeida, C., Kohen, R., Halpert, G. & Salmon-Divon M. Simulations of the NK Cell Immune Synapse Reveal that Activation Thresholds can be Established by Inhibitory Receptors Acting locally. *J. Immunol.* 187, 760-773 (2011).

The invention claimed is:
1. A method of analyzing a cell-cell interaction, the method comprising the steps of:
   (a) providing a microfluidic device capable of forming aqueous microdroplets in oil, the device comprising a translucent microdroplet array chamber, and providing an imaging microscope;
   (b) preparing a plurality of aqueous microdroplets in oil using the microfluidic device, at least a portion of the microdroplets each comprising three or more different types of individual cells in suspension and optionally one or more reagents for analyzing an interaction between said cells; wherein said three or more different types of individual cells comprise dendritic cells, T cells, and tumor cells wherein the microdroplets comprising three or more reagents that are capable of specifically labeling each of said three or more different types of cells;
   (c) directing the plurality of aqueous microdroplets into the microdroplet array chamber;
   (d) obtaining a series of images of the microdroplet array chamber over a period of time using the imaging microscope; and

(e) analyzing a cell-cell interaction using said images, wherein said analysis comprises detecting an interaction between a dendritic cell and a T cell followed by an interaction between said T cell and a tumor cell.

2. The method of claim 1, wherein the dendritic cells have been pre- incubated with one or more antigens from said tumor cells.

3. The method of claim 1, wherein the dendritic cells derive from a dendritic cell vaccine.

4. The method of claim 2, wherein the T cells and tumor cells both are obtained from a patient.

5. The method of claim 1, wherein the T cells are CAR T cells comprising a chimeric antigen receptor that is suspected of recognizing an antigen on the tumor cells.

6. The method of claim 1, wherein the analysis of cell-cell interactions is used to modify a patient therapy.

7. The method of claim 1, further comprising detecting death of said tumor cell after step (e).

* * * * *